United States Patent [19]

Avidan et al.

[11] Patent Number: 4,899,014

[45] Date of Patent: * Feb. 6, 1990

[54] UPGRADING PROPENE-ETHENE MIXTURES IN A TURBULENT FLUIDIZED CATALYST BED REACTOR

[76] Inventors: Amos A. Avidan, 2120 Stackhouse Dr., Yardley, Pa. 19067; David L. Johnson, 181 Concord Meeting Rd., Glen Mills, Pa. 19342; Jorge L. Soto, S-545 Inverness Apts., Westville, N.J. 08093

[*] Notice: The portion of the term of this patent subsequent to May 24, 2005 has been disclaimed.

[21] Appl. No.: 197,546

[22] Filed: May 23, 1988

Related U.S. Application Data

[63] Continuation-in-part of Ser. No. 6,407, Jan. 23, 1987, Pat. No. 4,746,762.

[51] Int. Cl.$^4$ .............................................. C07C 2/12
[52] U.S. Cl. ..................... 585/533; 585/415; 585/417
[58] Field of Search ................. 585/415, 417, 533

[56] References Cited

U.S. PATENT DOCUMENTS

| | | | |
|---|---|---|---|
| 3,907,663 | 9/1975 | Owen | 585/415 |
| 4,046,825 | 1/1978 | Owen et al. | 585/700 |
| 4,100,218 | 7/1978 | Chen et al. | 585/310 |
| 4,138,440 | 2/1979 | Chang et al. | 585/640 |
| 4,254,295 | 3/1981 | Tabak | 585/533 |
| 4,283,273 | 8/1981 | Owen | 585/415 |
| 4,417,086 | 11/1983 | Miller | 585/530 |
| 4,417,087 | 11/1983 | Miller | 585/530 |
| 4,517,396 | 5/1985 | Hoek et al. | 585/415 |
| 4,543,435 | 9/1985 | Gould et al. | 585/330 |
| 4,547,616 | 10/1985 | Avidan et al. | 585/640 |
| 4,579,999 | 4/1986 | Gould et al. | 585/312 |
| 4,605,807 | 8/1986 | Mazurek | 585/517 |
| 4,642,403 | 2/1987 | Hyde et al. | 585/415 |
| 4,689,205 | 8/1987 | Gould et al. | 585/312 |
| 4,746,762 | 5/1988 | Avidan et al. | 585/415 |

FOREIGN PATENT DOCUMENTS 2156381 10/1985 United Kingdom ................ 585/415

*Primary Examiner*—Asok Pal
*Attorney, Agent, or Firm*—Alexander J. McKillop; Charles J. Speciale; L. Gene Wise

[57] ABSTRACT

A fluidized bed catalytic process for conversion of propene-rich light olefinic gas feedstock comprising at least 2 mol % ethene and having a $C_3:C_2$ molar ratio of at least about 2:1 to produce hydrocarbons rich in $C_4^+$ aliphatics and aromatics, comprising maintaining a turbulent fluidized bed in a reactor operating at a moderate pressure in the range from about 400 to 2500 kPa, and temperature of about 315° to 510° C., the catalyst having an apparent particle density of about 0.9 to 1.6 g/cm$^3$, a size range of about 1 to 150 microns, and average catalyst particle size of about 20 to 100 microns containing about 10 to 25 weight percent of fine particles having a particle size less than 32 microns, by passing hot feedstock vapor upwardly through the fluidized catalyst bed at a superficial fluid velocity of about 0.3 to 2 meters per second. Hydrocarbon product is recovered containing a major amount of $C_5^+$ hydrocarbons and containing $C_3$–$C_5$ alkanes and alkenes in the ratio of about 0.1:1 to 200:1 and preferably at a reaction severity index (R.I.) of about 0.2:1 to 5:1.

16 Claims, 3 Drawing Sheets

UPGRADING PROPENE-ETHENE MIXTURES IN A TURBULENT FLUIDIZED CATALYST BED REACTOR

CROSS-REFERENCE TO RELATED APPLICATIONS

This application is a continuation-in-part of U.S. Patent application Ser. No. 006,407, filed Jan. 23, 1987, now U.S. Pat. No. 4,746,762.

BACKGROUND OF THE INVENTION

This invention relates to a catalytic technique for upgrading light olefin gas to heavier hydrocarbons. In particular, it provides a continuous process for oligomerizing ethene/propene-containing olefinic light gas feedstock, optionally containing paraffins, such as propane, or other lower alkanes. The inventive process is employed advantageously in conjunction with light hydrocarbon gas recovery operations associated with FCC refinery units to produce $C_4+$hydrocarbons, such as olefinic liquid fuels, isobutane, aromatics and other useful products. Propene (propylene, $C_3H_6$) and ethene (ethylene, $C_2H_4$)-containing gases, such as petroleum cracking offgas, are useful feedstocks herein.

Developments in zeolite catalysis and hydrocarbon conversion processes have created interest in utilizing olefinic feedstocks for producing $C_5+$gasoline, diesel fuel, etc. In addition to basic chemical reactions promoted by ZSM-5 type zeolite catalysts, a number of discoveries have contributed to the development of new industrial processes. These are safe, environmentally acceptable processes for utilizing feedstocks that contain lower olefins, especially $C_2-C_4$ alkenes. Conversion of $C_2-C_4$ alkenes and alkanes to produce aromatics-rich liquid hydrocarbon products were found by Cattanach (US 3,760,024) and Yan et al (US 3,845,150) to be effective processes using the ZSM-5 type zeolite catalysts. In U.S. Pat. Nos. 3,960,978 and 4,021,502, Plank, Rosinski and Givens disclose conversion of $C_2-C_5$ olefins, alone or in admixture with paraffinic components, into higher hydrocarbons over crystalline zeolites having controlled acidity. Garwood et al have also contributed to the understanding of catalytic olefin upgrading techniques and improved processes as in U.S. Pat. Nos. 4,150,062, 4,211,640 and 4,227,992. The above-identified disclosures are incorporated herein by reference.

Conversion of lower olefins, especially propene and butenes, over HZSM-5 is effective at moderately elevated temperatures and pressures. The conversion products are sought as liquid fuels, especially the $C_5+$aliphatic and aromatic hydrocarbons. Product distribution for liquid hydrocarbons can be varied by controlling process conditions, such as temperature, pressure and space velocity. Gasoline ($C_5-C_{10}$) is readily formed at elevated temperature (e.g., up to about 400° C.) and moderate pressure from ambient to about 5500 kPa, preferably about 250 to 2900 kPa. Olefinic gasoline can be produced in good yield and may be recovered as a product or fed to a low severity, high pressure reactor system for further conversion to heavier distillate-range products. Distillate mode operation can be employed to maximize production of $C_{10}+$aliphatics by reacting the lower and intermediate olefins at high pressure and moderate temperature. Operating details for typical "MOGD" oligomerization units are disclosed in U.S. Pat. Nos. 4,456,779; 4,497,968 (Owen et al.) and 4,433,185 (Tabak), incorporated herein by reference. At moderate temperature and relatively high pressure, the conversion conditions favor distillate-range product having a normal boiling point of at least 165° C. (330° F.). Lower olefinic feedstocks containing $C_2-C_6$ alkenes may be converted selectively; however the low severity distillate mode conditions do not convert a major fraction of ethene. While propene, butene-1, and others may be converted to the extent of 50% to 95% in the lower severity moderate temperature distillate mode, only about 10% to 30% of the ethene component will be converted using HZSM-5 or similar acid zeolites. Many feedstocks of commercial interest, such as FCC offgas, dehydrogenation products, ethane cracking byproduct, etc., contain both ethene and hydrogen along with $H_2S$ and light aliphatics. Ethene can also be converted at moderate temperature with a bifunctional nickel catalyst.

It has been found that propene-rich olefinic light gas, particularly propene-enriched ethylenic fuel gas, can be upgraded to liquid hydrocarbons rich in olefinic gasoline, isobutane and aromatics by catalytic conversion in a turbulent fluidized bed of solid acid zeolite catalyst under high severity reaction conditions in a single pass or with recycle of gas product. This technique is particularly useful for upgrading FCC light gas, which usually contains significant amounts of ethene, propene, $C_2-C_4$ paraffins and hydrogen produced in cracking heavy petroleum oils or the like. By upgrading the by-product light gas, gasoline yield of FCC units can be significantly increased. Accordingly, it is a primary object of the present invention to provide a novel technique for upgrading propene-rich light gas.

SUMMARY OF THE INVENTION

An improvement has been discovered nn the process for continuous conversion of ethene-containing light hydrocarbon feedstock to heavier hydrocarbon products wherein the feedstock is contacted at elevated temperature with a fluidized bed of zeolite catalyst under conversion conditions while maintaining the fluidized catalyst bed in a vertical reactor column having a turbulent reaction zone by passing feedstock gas upwardly through the reaction zone at a velocity greater than dense bed transition velocity to a turbulent regime and less than transport velocity for the average catalyst particle. A portion of coked catalyst withdrawn from the reaction zone is oxidatively regenerated catalyst and returned to the reaction zone at a rate to control catalyst activity whereby $C_3-C_5$ alkane:alkene weight ratio in the hydrocarbon product is maintained at about 0.1:1 to 20:1 under conditions of reaction severity to effect feedstock conversion. The present improvement comprises enriching olefinic feedstock with a propene-propane mixture to provide a molar ratio of propene:ethene of at least 2:1, thereby obtaining increased throughput, gasoline yield and $C_4+$hydrocarbon product.

THE DRAWINGS

DESCRIPTION OF PREFERED EMBODIMENTS

Description of Catalysts

Figure 1:
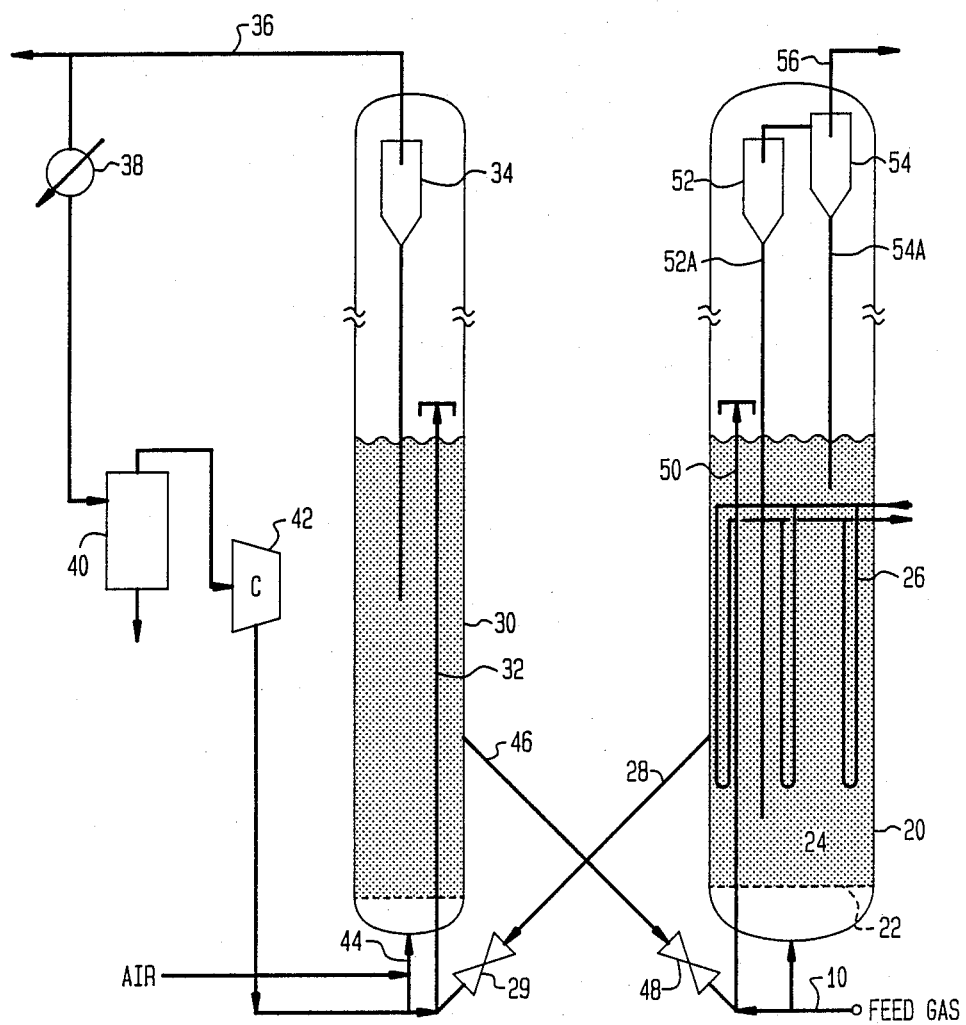
FIG. 1 is a schematic view of a fluidized bed reactor system according to the present invention.

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, B or Fe, within the zeolitic framework. These medium pore zeolites are favored for acid catalysis; however, the advantages of ZSM-5 structures may be utilized by employing highly siliceous materials or crystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

The oliqomerization catalysts preferred for use herein include the medium pore (i.e., about 5–7A) shape-selective crystalline aluminosilicate zeolites having a silica-to-alumina ratio of at least 12, a constraint index of about 1 to 12 and acid cracking activity of about 10–250. In the fluidized bed reactor the coked catalyst may have an apparent activity (alpha value) of about 10 to 80 under the process conditions to achieve the required degree of reaction severity. Representative of the ZSM-5 type zeolites are ZSM-5, ZSM-11, ZSM-12, ZSM-22, ZSM-23, ZSM-35 and ZSM-48. ZSM-5 is disclosed in U.S. Pat. No. 3,702,886 and U.S. Pat. No. Re. 29,948. Other suitable zeolites are disclosed in U.S. Pat. Nos. 3,709,979; 3,832,449; 4,076,979; 4,076,842; 4,046,839; and 4,579,999. The disclosures of these patents are incorporated herein by reference. While suitable zeolites having a coordinated metal oxide to silica molar ratio of 20:1 to 200:1 or higher may be used, it is advantageous to employ a standard ZSM-5 having a silica alumina molar ratio of about 25:1 to 70:1, suitably modified. A typical zeolite catalyst component having Bronsted acid sites may consist essentially of aluminosilicate ZSM-5 zeolite with 5 to 95 wt. % silica and/or alumina binder.

These siliceous zeolites may be employed in their acid forms ion exchanged or impregnated with one or more suitable metals, such as Ga, Pd, Zn, Ni, Co and/or other metals of Periodic Groups III to VIII. The zeolite may include a hydrogenation-dehydrogenation component (sometimes referred to as a hydrogenation component) which is generally one or more metals of group IB, IIB, IIIB, VA, VIA or VIIIA of the Periodic Table (IUPAC), especially aromatization metals, such as Ga, Pd, etc. Useful hydrogenation components include the noble metals of Group VIIIA, especially platinum, but other noble metals, such as palladium, gold, silver, rhenium or rhodium, may also be used. Base metal hydrogenation components may also be used, especially nickel, cobalt, molybdenum, tungsten, copper or zinc. The catalyst materials may include two or more catalytic components, such as a metallic oligomerization component (e.g., ionic $Ni^{+2}$, and a shape-selective medium pore acidic oligomerization catalyst, such as ZSM-5 zeolite) which components may be present in admixture or combined in a unitary bifunctional solid particle. It is possible to utilize an ethene dimerization metal or oligomerization agent to effectively convert feedstock ethene in a continuous reaction zone.

Certain of the ZSM-5 type medium pore shape selective catalysts are sometimes known as pentasils. In addition to the preferred aluminosilicates, the borosilicate ferrosilicate and "silicalite" materials may be employed. It is advantageous to employ a standard ZSM-5 having a silica:alumina molar ratio of 25:1 to 70:1 with an apparatus alpha value of 3–80 to convert 60 to 100 percent, preferably at least 70%, of the olefins in the feedstock.

ZSM-5 type pentasil zeolites are particularly useful in the process because of their regenerability, long life and stability under the extreme conditions of operation. Usually the zeolite crystals have a crystal size from about 0.01 to over 2 microns or more, with 0.02–1 micron being preferred. In order to obtain the desired particle size for fluidization in the turbulent regime, the zeolite catalyst crystals are bound with a suitable inorganic oxide, such as silica, alumina, etc. to provide a zeolite concentration of about 5 to 95 wt. %. In the description of preferred embodiments a 25% H-ZSM-5 catalyst contained within a silica-alumina matrix and having a fresh alpha value of about 80 is employed unless otherwise stated.

Particle size distribution can be a significant factor in achieving overall homogeneity in turbulent regime fluidization. It is desired to operate the process with particles that will mix well throughout the bed. Large particles having a particle size greater than 250 microns should be avoided, and it is advantageous to employ a particle size range consisting essentially of 1 to 150 microns. Average particle size is usually about 20 to 100 microns, preferably 40 to 80 microns. Particle distribution may be enhanced by having a mixture of larger and smaller particles within the operative range, and it is particularly desirable to have a significant amount of fines. Close control of distribution can be maintained to keep about 10 to 25 wt % of the total catalyst in the reaction zone in the size range less than 32 microns. This class of fluidizable particles is classified as Geldart Group A. Accordingly, the fluidization regime is controlled to assure operation between the transition velocity and transport velocity. Fluidization conditions are substantially different from those found in non-turbulent dense beds or transport beds.

Process Operation

In this description, metric units and parts by weight are employed unless otherwise stated.

The preferred feedstock contains $C_2$–$C_6$ alkenes (mono-olefin) including at least 2 mole % ethene, wherein the total $C_2$–$C_3$ alkenes are in the range of about 10 to 100 wt%. Non-deleterious components, such as methane and other paraffins and inert gases, may be present. Some of the paraffins in the feed will also convert to $C_4+$ hydrocarbons, depending on reaction conditions and the catalyst employed.

A particularly useful feedstock is a light gas by-product of FCC gas oil cracking units containing typically 10–60 mol % $C_2$–$C_4$ olefins and 5–35 mol % $H_2$ with varying amounts of $C_1$–$C_3$ paraffins and inert gas, such as $N_2$. The process may be tolerant of a wide range of lower alkanes, from 0 to 90%. Feedstocks may contain more than 50 wt. % $C_1$–$C_4$ lower aliphatic hydrocarbons, but should contain sufficient olefins to provide total olefinic partial pressure of at least 50 kPa. Under the reaction severity conditions employed in the present invention, lower alkanes, such as propane optionally cofed with propene from FCC light gas recovery, may be partially converted to $C_4^+$ products.

The desired products are $C_4$ to $C_9$ hydrocarbons, which will comprise at least 50 wt. % of the recovered product, preferably 80% or more. While olefins may be a predominant fraction of the $C_4^+$ reaction effluent, up to 45% butenes, pentenes, hexenes, heptenes, octenes, nonenes and their isomers; it is desired to upgrade the feedstock to high octane gasoline containing aromatics, preferably at least 10% by weight.

The reaction severity conditions can be controlled to optimize yield of $C_4$-$C_9$ aliphatic hydrocarbons. It is understood that aromatics and light paraffin production is promoted by those zeolite catalysts having a high concentration of Bronsted acid reaction sites. Accordingly an important criterion is selecting and maintaining catalyst inventory to provide either fresh catalyst having acid activity or by controlling catalyst deactivation and regeneration rates to provide an apparent average alpha value of about 3 to 80.

Reaction temperatures and contact time are also significant factors in the reaction severity, and the process parameters are followed to give a substantially steady state condition wherein the reaction severity index (R.I.) is maintained within those operating conditions which yield a desired weight ratio of propane to propene. While this index may vary greatly in the presence of added propane in the feedstock, eg-from about 0.1 to 200, it is preferred to operate the steady state fluidized bed unit to hold the R.I. at about 0.2:1 to 5:1, when measured in the substantial absence of added propane. While reaction severity is advantageously determined by the weight ratio of propane:propene in the gaseous phase, it may also be approximated by the analogous ratios of butanes:butenes, pentanes:pentenes, or the average of total reactor effluent alkanes:alkenes in the $C_3$-$C_5$ range, as depicted graphically in FIG. 5.

Figure 5:
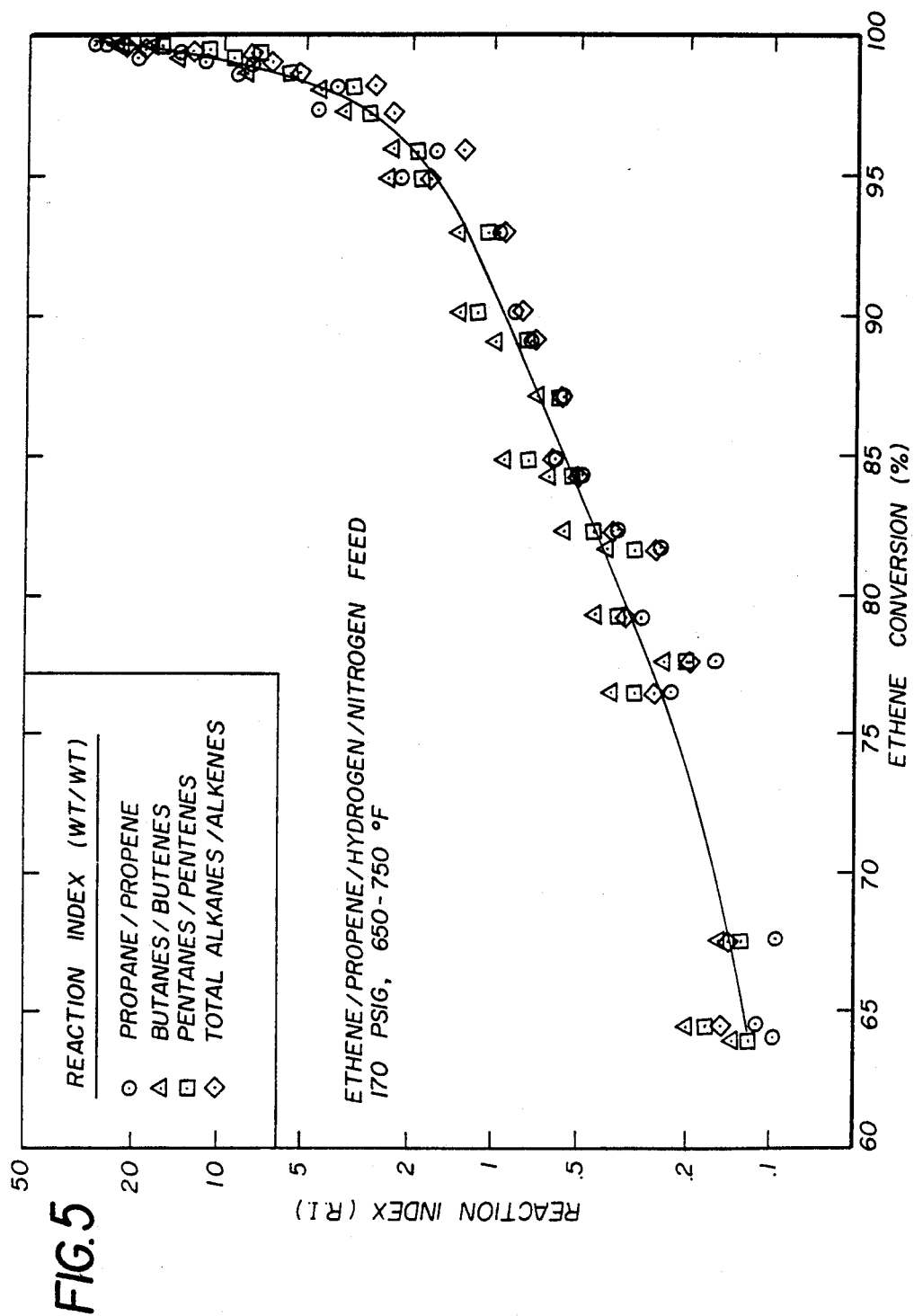
FIG. 5 is a semilog plot comparing $C_3$–$C_5$ alkane:alkene.

FIG. 5 shows the close relationship between R.I. value for $C_3$, $C_4$ and $C_5$ aliphatics and total alkane:alkene ratio. These values are shown in the range of 0.1 to 50 with typical $C_2$-$C_3$ olefinic feedstock in the substantial absence of added propane in the feedstock. The optimum value will depend upon the exact catalyst composition, feedstock and reaction conditions; however, the typical ethene/propene-rich light gas mixtures used in the examples herein and similar cracking process off-gas can be optionally upgraded to the desired aliphatic-rich gasoline by keeping the R.I. at about 1.

The olefinic feedstream may be enriched by addition of propane to increase the production of $C_4^+$ product. Propane containing streams, such as $C_3$-$C_4$ LPG and various refinery fractions can be employed to supplement the olefinic feedstock. Suitable $C_2$-$C_4$ aliphatic mixtures containing 20 to 85 wt. % propane may enhance olefinic feedstocks of 15 to 80% mono-alkene. Since propane conversion is incomplete under ordinary operating conditions, this addition can raise the apparent $C_3$ R.I. value above 50:1.

The use of fluidized bed catalysis permits the conversion system to be operated at low pressure drop, which in an economically practical operation can provide a total operating pressure of about 200 to 2500 kPa, preferably at least 400 kPa. Another important advantage is the close temperature control that is made possible by turbulent regime operation, wherein the uniformity of conversion temperature can be maintained within close tolerances, often less than 25° C. Except for a small zone adjacent the bottom gas inlet, the midpoint measurement is representative of the entire bed, due to the thorough mixing achieved.

In a typical process, the olefinic feedstock is converted in a catalytic reactor under oligomerization conditions and moderate pressure (i.e., 400 to 2000 kPa) to produce at least 6% isobutane and a predominantly liquid product consisting essentially of $C_4^+$ hydrocarbons rich in gasoline-range olefins and aromatics.

Referring now to FIG. 1, feed gas rich in $C_2$-$C_3$ olefins passes under pressure through conduit 10, with the main flow being directed through the bottom inlet of reactor vessel 20 for distribution through grid plate 22 into the fluidization zone 24. Here the feed gas contacts the turbulent bed of finely divided catalyst particles. Reactor vessel 10 is shown provided with heat exchange tubes 26, which may be arranged as several separate heat exchange tube bundles so that temperature control can be separately exercised over different portions of the fluid catalyst bed. The bottoms of the tubes are spaced above feed distributor grid 22 sufficiently to be free of jet action by the charged feed through the small diameter holes in the grid.

Alternatively, reaction heat can be partially or completely removed by using cold feed. Baffles may be added to control radial and axial mixing. Although depicted without baffles, the vertical reaction zone can contain open end tubes above the grid for maintaining hydraulic constraints, as disclosed in U.S. Pat. No. 4,251,484 (Daviduk and Haddad). Heat released from the reaction can be controlled by adjusting feed temperature in a known manner.

Catalyst outlet means 28 is provided for withdrawing catalyst from above bed 24 and passed for catalyst regeneration in vessel 30 via control valve 29. The partially deactivated catalyst is oxidatively regenerated by controlled contact with air or other regeneration gas at elevated temperature in a fluidized regeneration zone to remove carbonaceous deposits and restore acid acitivity. The catalyst particles are entrained in a lift gas and transported via riser tube 32 to a top portion of vessel 30. Air is distributed at the bottom of the bed to effect fluidization, with oxidation byproducts being carried out of the regeneration zone through cyclone separator 34, which returns any entrained solids to the bed. Flue gas is withdrawn via top conduit 36 for disposal; however, a portion of the flue gas may be recirculated via heat exchanger 38, separator 40, and compressor 42 for return to the vessel with fresh oxidation gas via line 44 and as lift gas for the catalyst in riser 32.

Regenerated catalyst is passed to the main reactor 20 through conduit 46 provided with flow control valve 48. The regenerated catalyst may be lifted to the catalyst bed with pressurized feed gas through catalyst return riser conduit 50.

Since the amount of regenerated catalyst passed to the reactor is relatively small, the temperature of the regenerated catalyst does not upset the temperature constraints of the reactor operations in significant amount. A series of sequentially connected cyclone separators 52, 54 are provided with diplegs 52 A, 54 A to return any entrained catalyst fines to the lower bed. These separators are positioned in an upper portion of the reactor vessel comprising dispersed catalyst phase 24. Filters, such as sintered metal plate filters, can be used alone or in conjunction with cyclones. The product effluent separated from catalyst particles in the cyclone separating system is then withdrawn from the reactor vessel 20 through top gas outlet means 56. The recovered hydrocarbon product comprising $C_5$+olefins and/or aromatics, paraffins and naphthenes is thereafter processed as required to provide a desired gasoline or higher boiling product.

Under optimized process conditions the turbulent bed has a superficial vapor velocity of about 0.3 to 2 meters per second (m/s). At higher velocities, entrainment of fine particles may become excessive and beyond about 3 m/s the entire bed may be transported out of the reaction zone. At lower velocities, the formation of large bubbles or gas voids can be detrimental to conversion. Even fine particles cannot be maintained effectively in a turbulent bed below about 0.1 m/sec.

A convenient measure of turbulent fluidization is the bed density. A typical turbulent bed has an operating density of about 100 to 500 kg/m³, preferably about 300 to 500 kg/m³, measured at the bottom of the reaction zone, becoming less dense toward the top of the reaction zone, due to pressure drop and particle size differentiation. This density is generally between the catalyst concentration employed in dense beds and the dispersed transport systems. Pressure differential between two vertically spaced points in the reactor column can be measured to obtain the average bed density at such portion of the reaction zone. For instance, in a fluidized bed system employing ZSM-5 particles having an apparent packed density of 750 kg/m³ and real density of 2430 kg/m³, an average fluidized bed density of about 300 to 500 kg/m³ is satisfactory.

By virtue of the turbulence experienced in the turbulent regime, gas-solid contact in the catalytic reactor is improved, providing high ethene/propene conversion in the range of about 70–95+%, enhanced selectivity and temperature uniformity. One main advantage of this technique is the inherent control of bubble size and characteristic bubble lifetime. Bubbles of the gaseous reaction mixture are small, random and short-lived, thus resulting in good contact between the gaseous reactants and the solid catalyst particles.

A significant difference between the process of this invention and conversion processes of the prior art is that operation in the turbulent fluidization regime is optimized to product high octane $C_5$+liquid in good yield. The weight hourly space velocity and uniform contact provides a close control of contact time between vapor and solid phases, typically about 3 to 15 seconds. Another advantage of operating in such a mode is the control of bubble size and life span, thus avoiding large scale gas by-passing in the reactor.

As the superficial gas velocity is increased in the dense bed, eventually slugging conditions occur and with a further increase in the superficial gas velocity the slug flow breaks down into a turbulent regime. The transition velocity at which this turbulent regime occurs appears to decrease with particle size. The turbulent regime extends from the transition velocity to the so-called transport velocity, as described by Avidan et al in U.S. Pat. No. 4,547,616, incorporated herein by reference. As the transport velocity is approached, there is a sharp increase in the rate of particle carryover, and in the absence of solid recycle, the bed could empty quickly.

Several useful parameters contribute to fluidization in the turbulent regime in accordance with the process of the present invention. When employing a ZSM-5 type zeolite catalyst in fine powder form such a catalyst should comprise the zeolite suitably bound or impregnated on a suitable support with a solid density (weight of a representative individual particle divided by its apparent "outside" volume) in the range from 0.6–2 g/cc, preferably 0.9–1.6 g/cc. The catalyst particles can be in a wide range of particle sizes up to about 250 microns, with an average particle size between about 20 and 100 microns, preferably between 40 and 80 microns. When these solid particles are placed in a fluidized bed where the superficial fluid velocity is 0.3–2 m/s, operation in the turbulent regime is obtained. Those skilled in the art will appreciate that at higher pressures, a lower gas velocity may be employed to ensure operation in the turbulent fluidization regime.

The reactor can assume any technically feasible configuration, but several important criteria should be considered. The bed of catalyst in the reactor can be at least about 5–20 meters in height, preferably about 7–9 meters. Fine particles may be included in the bed, especially due to attrition, and the fines may be entrained in the product gas stream. A typical turbulent bed may have a catalyst carryover rate up to about 1.5 times the reaction zone inventory per hour. If the fraction of fines becomes large, a portion of the carryover can be removed from the system and replaced by larger particles. It is feasible to have a fine particle separator, such as a cyclone and/or filter means, disposed within or outside the reactor shell to recover catalyst carryover and return this fraction continuously to the bottom of the reaction zone for recirculation at a rate of about one catalyst inventory per hour. Optionally, fine particles carried from the reactor vessel entrained with effluent gas can be recovered by a high operating temperature sintered metal filter.

This process can be used with any process stream which contains sufficient light olefins and paraffins. For example, it can be used to process FCC by-product fuel gas, which typically contains about 10 to 40 wt. % total ethene, and is enriched to contain at least about 3 parts by weight of propene per part of ethene (ie-2:1 to 40:1 molar ratio). Experimental runs are performed using a ZSM-5 catalyst to demonstrate the inventive process. The fluidized bed unit can be operated over a wide range of process variables and catalyst activity.

Reactor Operation

A typical reactor unit employs a temperature-controlled catalyst zone with indirect heat exchange and/or adjustable gas quench, whereby the reaction exotherm can be carefully controlled to prevent excessive temperature above the usual operating range of about 315° C. to 510° C., preferably at average reactor temperature of 315° C. to 430° C. Energy conservation in the system may utilize at least a portion of the reactor exotherm heat value by exchanging hot reactor effluent with feedstock and/or recycle streams. Optional heat exchangers may recover heat from the effluent stream prior to fractionation. Part of all of the reaction heat can be removed from the reactor without using the indirect heat exchange tubes by using cold feed, whereby reactor temperature can be controlled by adjusting feed temperature. The internal heat exchange tubes can still be used as internal baffles which lower reactor hydraulic diameter, and axial and radial mixing.

The weight hourly space velocity (WHSV, based on total olefins in the fresh feedstock is about 0.1–5 WHSV. Typical product fractionation systems are described in U.S. Pat. Nos. 4,456,779 and 4,504,693 (Owen, et al.). Typical results of ethene-rich catalysis obtained in a fluid bed reactor are shown in Examples 1–3.

| Reactor Conditions: | |
|---|---|
| Temperature | 370° C. |
| Pressure | 410 kPA |
| Olefin-WHSV | 0.5 |
| No Recycle | |
| Feed Composition, wt. % | |
| Hydrogen | 10.7 |
| Ethene | 89.3 |
| Product Yields | |
| Methane | 0.1 |
| Ethane | 1.9 |
| Ethene | 11.7 |
| Propane | 7.3 |
| Propene | 5.0 |
| Isobutane | 10.6 |
| n-Butane | 4.4 |
| Butenes | 7.6 |
| $C_5^+$ Hydrocarbons | 51.4 |
| $C_5^+$ Hydrocarbon Properties | |
| R + O Octane | 93.2 |
| Specific Gravity | 0.74 |

| Reactor Conditions: | |
|---|---|
| Temperature | 370° C. |
| Pressure | 1200 kPA |
| Olefin-WHSV | 0.4 |
| No Recycle | |
| Feed Composition, wt. % | |
| Nitrogen | 65.8 |
| Hydrogen | 0.8 |
| Ethene | 14.7 |
| Propene | 18.7 |
| Product Yields | |
| Methane | 0.1 |
| Ethane | 1.4 |
| Ethene | 3.6 |
| Propane | 8.9 |
| Propene | 2.8 |
| Isobutane | 12.8 |
| n-Butane | 6.0 |
| Butenes | 5.7 |
| $C_5^+$ Hydrocarbons | 58.7 |
| $C_5^+$ Hydrocarbon Properties | |
| R + O Octane | 93.2 |
| Specific Gravity | 0.74 |

EXAMPLE 3

| Reactor Conditions: | |
|---|---|
| Temperature | 370° C. |
| Pressure | 1200 kPA |
| Olefin-WHSV | 0.4 |
| Recycle ratio, Mol/Mole | 1.4 |
| Feed Composition, wt. % | |
| Nitrogen | 65.8 |
| Hydrogen | 0.8 |
| Ethene | 14.7 |
| Propene | 18.7 |
| Product Yields | |
| Methane | 0.1 |
| Ethane | 0.7 |
| Ethene | 6.0 |
| Propane | 4.7 |
| Propene | 3.0 |
| Isobutane | 9.9 |
| n-Butane | 3.6 |
| Butenes | 6.3 |
| $C_5^+$ Hydrocarbons | 65.7 |
| $C_5^+$ Hydrocarbon Properties | |
| R + O Octane | 90.3 |

| -continued | |
|---|---|
| Specific Gravity | 0.73 |

Example 1 is for a feed containing only ethene and hydrogen. Example 2 is for a feed containing nitrogen, hydrogen, ethene and propene. $C_4^+$ yields will be higher, as some of the alkanes convert. Example 3 is similar to Example 2, but a substantial portion of the $C_4^-$ product is recycled back to the reactor. $C_5^+$ yields are higher and catalyst makeup requirements are lower for Example 3 compared to Example 2. Higher isobutane yields, and higher gasoline octane numbers are possible at higher temperatures, lower pressures, and higher catalyst activity.

The produced isobutane, usually more than 5 wt. %, may have significant impact on potential alkylate yield, depending on the supply situation of isobutane in a petroleum refinery. The maximum yield ($C_5^+$ plus alkylates) may be achieved at a conversion temperature between 360° to 415° C. The flexibility of the fluid bed for controlling the reactor temperature under exothermic reaction conditions allows an easy adjustment for achieving the optimal yield structure. The proposed fuel gas conversion unit can fit into an existing FCC gas plant, with appropriate amine scrubbing to remove most of the deleterious sulfur compounds, such as $H_2S$.

EXAMPLE 4

To demonstrate the effect of propene enrichment, a continuous fluid-bed olefin upgrading unit is operated with a feed which contains a minor amount ethylene and part or all of the $C_3$ propane/propylene stream from a refinery cracking complex. The $C_3$ may be the only feed or may be mixed with the cracking complex fuel gas stream. The propylene converts quite readily at MOG conditons (315–510° C., 180 psig, and 0.8 WHSV, for example) to produce mainly $C_5$+gasoline, with octane ranging from 90 to 100 R+O, depending on the reactor temperature. Gasoline yield is typically 2-5 wt. % higher than for fuel gas feed alone in the substantial absence of $C_3$ components, while the octane quality is about the same under similar operating conditions.

Typical feedstock is a dilute ethylene stream, usually the fuel gas from the refinery cracking complex. This stream will normally contain some propylene in addition to ethylene. Typical weight ratios of ethylene to propylene are 3:1 to 1:1. The propylene present in this stream converts readily. The present invention involves adding additional propylene, typically from the refinery cracking complex $C_3$ stream, to bring the ethylene-propylene weight ratio down to 1:3 to 1:4, which may be expressed as a $C_3:C_2$ molar ratio greater than 2:1. Reactor space velocity (WHSV on total olefins) in feed can be at least doubled by adding additional propylene without significantly affecting the conversion of ethylene present in the fuel gas.

Figure 2:
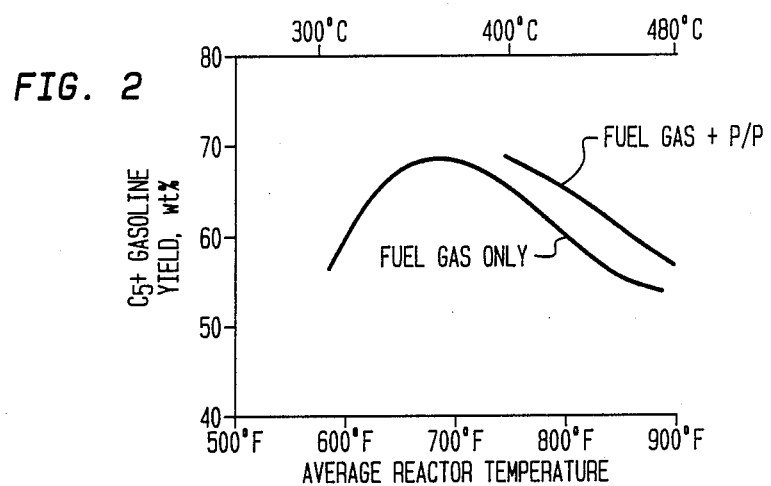
FIG. 2 is a graphic plot showing product yields vs. reaction temperature.
Figure 3:
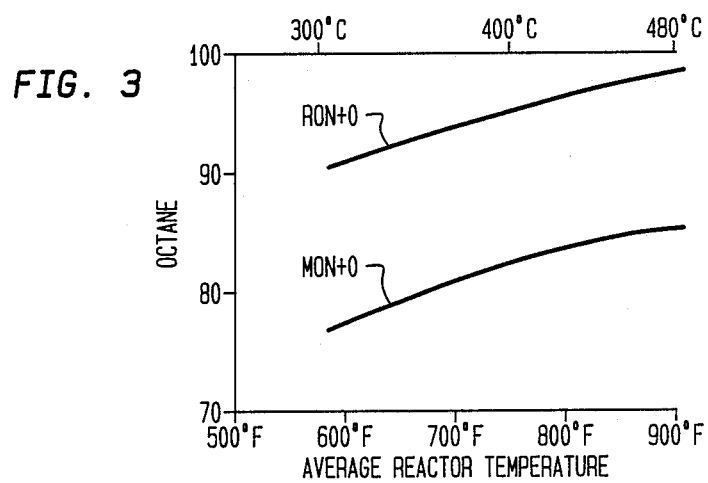
FIG. 3 shows corresponding liquid product octane vs temperature.

Table 4 shows results from a fluid-bed upgrading plant for adding additonal propylene to a simulated fuel gas mixture. In this example, the reactor temperature, fuel gas feed rate, and catalyst inventory are held constant. Adding the propylene (simulating a commercial $C_3$ stream), results in a doubling of the WHSV on feed olefins. Despite this increase in WHSV, ethylene conversion only decreases by 1%, and gasoline yield increased by 4% without a change in the gasoline octane quality. The effect of adding the $C_3$ stream to the fuel gas feed at various temperatures is shown in FIGS. 2 and 3. As shown in FIG. 2, the additional propylene results in about a 2-5% increase in gasoline yield, and the yield for both feeds decreases with increasing temperature. Product octane increases with temperature; therefore, the most desirable operating point will depend on the relative value of yield versus octane in the refinery.

TABLE 4
Effect of Propene Addition

| Feed | Fuel Gas Only | Fuel Gas + Propene | |
|---|---|---|---|
| Ethene/Propene Weight Ratio | 47/53 | 23/77 | |
| WHSV on Total Olefins, $Hr^{-1}$ | 0.36 | 0.74 | |
| WHSV on Ethene, $Hr^{-1}$ | 0.17 | 0.17 | |
| Reactor Temp., °C. (°F.) | 427 (800) | 427 (800) | |
| Avg. Reactor Vel., m/s | 0.83 | 1.0 | |
| Partial Pressures, psia | | | |
| Ethene | 24.5 | 19.8 | Incremental Yield on Added Propene, wt. % |
| Propene | 17.0 | 39.6 | |
| Conversions, wt. % | | | |
| Ethene | 95.2 | 94.3 | — |
| Propene | 92.1 | 96.0 | 97.9 |
| Yields on Olefin Feed, Wt. % | | | |
| Methane | 0.2 | 0.1 | 0.0 |
| Ethane | 0.7 | 0.4 | 0.1 |
| Ethylene | 2.3 | 1.3 | 0.4 |
| Propane | 8.5 | 7.6 | 6.7 |
| Propene | 4.2 | 3.1 | 2.1 |
| n-Butane | 5.6 | 6.0 | 6.4 |
| i-Butane | 12.3 | 11.8 | 11.3 |
| Butenes | 6.1 | 5.3 | 4.5 |
| $C_5^+$ Gasoline | 60.1 | 64.4 | 68.5 |
| $C_5^+$ Gasoline Properties | | | |
| RON + O | 96.7 | 96.8 | |
| MON + O | 84.0 | 83.7 | |
| Specific Gravity | 0.751 | 0.748 | |
| RVP | 7.3 | 7.3 | |

Figure 4:
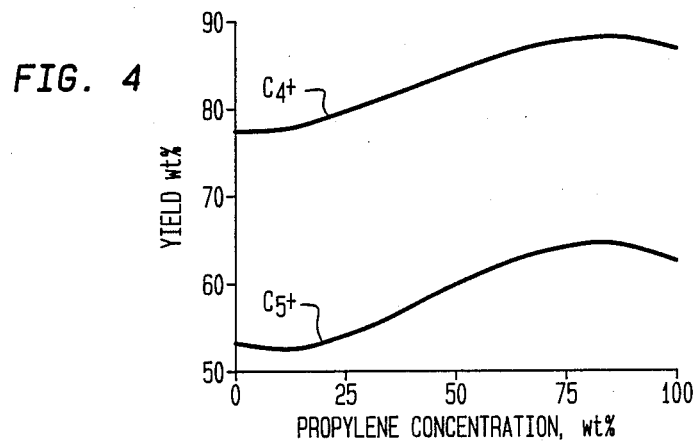
FIG. 4 shows yields for various mixtures of propene and ethene in feedstock olefin.

FIG. 4 depicts graphically the synergism in yields for mixtures of ethene and propene. A binary mixture containing 75-80 wt. % propene gives the optimum yield, corresponding to a molar ratio of $C_3:C_2$ of about 2:1 to 3:1. This proportion is approximately that of a typical mixture of FCC fuel gas and $C_3$ streams.

The use of a fluid-bed reactor in this process offers several advantages over a fixed-bed reactor. Due to continuous catalyst regeneration, fluid-bed reactor operation will not be adversely affected by oxygenate, sulfur and/or nitrogen containing contaminants presented in FCC fuel gas. In addition, the high isobutane yield in a fluid-bed reactor operation could be a significant advantage in isobutane short refineries.

The reaction temperature can be controlled by adjusting the feed temperature so that the enthalphy change balances the heat of reaction. The feed temperature can be adjusted by a feed preheater, heat exchange between the feed and the product, or a combination of both. Once the feed and product compositions are determined using, for example, an on-line gas chromatograph, the feed temperature needed to maintain the desired reactor temperature, and consequent olefin conversion, can be easily calculated from a heat balance of the system. In a commercial unit this can be done automatically by state-of-the-art control techniques.

While the invention has been shown by describing preferred embodiments of the process, there is no intent to limit the inventive concept, except as set forth in the following claims.

We claim:

1. A fluidized bed catalytic process for conversion of propene-rich light olefinic gas feedstock comprising at least 2 mol % ethene and having a $C_3:C_2$ olefin molar ratio of at least about 2:1 to produce hydrocarbons rich in $C_4^+$ aliphatics and aromatics, comprising the steps of: maintaining a turbulent fluidized bed in a reactor operating at a pressure in the range from about 400 to 2500 kPa, and temperature of about 315 to 510° C., said catalyst being a particulate zeolite having a silica:alumina molar ratio in the range from about 20:1 to about 200:1, an apparent particle density of about 0.9 to 1.6 g/cm$^3$, a size range of about 1 to 150 microns, and average catalyst particle size of about 20 to 100 microns containing about 10 to 25 weight percent of fine particles having a particle size less than 32 microns;
passing hot light olefinic gas feedstock upwardly through the fluidized catalyst bed in a single pass under turbulent flow conditions which provide reaction severity conditions sufficient to convert at least about 70% of feedstock ethene and propene;
maintaining turbulent fluidized bed conditions at a superficial feedstock velocity of about 0.3 to 2 meters per second through the reactor bed; and
recovering hydrocarbon product containing a major amount of $C_4^+$ hydrocarbons, at least 6% isobutane, and containing propane and propene in a ratio in the range from about 0.1:1 to 5:1.

2. The process of claim 1 wherein the catalyst comprises a siliceous metallosilicate acid zeolite having the structure of ZSM-5 zeolite and a silica:alumina ratio in the range from about 25:1 to 70:1.

3. The process of claim 1 wherein the feedstock consists essentially of light cracking gas comprising at least 75 to 80 weight percent propene and about 2 to 25 wt. % ethene.

4. In the process for continuous conversion of ethene-containing light hydrocarbon feedstock to heavier hydrocarbon products wherein the feedstock is contacted at elevated temperature with a fluidized bed of zeolite catalyst under conversion conditions while maintaining the fluidized catalyst bed in a vertical reactor column having a turbulent reaction zone by passing feedstock gas upwardly through the reaction zone at a velocity greater than dense bed transition velocity to a turbulent regime and less than transport velocity for the average catalyst particle, and withdrawing a portion of coked catalyst from the reaction zone, oxidatively regenerating the withdrawn catalyst and returning regenerated catalyst to the reaction zone at a rate to control catalyst activity whereby $C_3$–$C_5$ alkane:alkene weight ratio in the hydrocarbon product is maintained at about 0.1:1 to 200:1 under conditions of reaction severity to effect feedstock conversion; the improvement which comprises:
enriching olefinic feedstock with a propene-propane mixture to provide a molar ratio of propene:ethene or at least 2:1, thereby increasing yields of isobutane and $C_5^+$ gasoline.

5. A continuous process for conversion of propene-enriched light hydrocarbon feedstock comprising fuel gas from fluid catalytic cracking of petroleum oil to produce heavier hydrocarbon products wherein feedstock containing ethene and propene in a weight ratio of about 1:3 to 1:4 is contacted with a fluidized bed of medium pore shape selective zeolite catalyst particles under conversion conditions, comprising the steps of:

passing said feedstock upwardly through the fluidized bed in a vertical reactor column having a turbulent reaction zone, while maintaining a superficial velocity in the range from 0.3 to 2 meters per second to maintain a fluidized reaction zone containing finely divided solid catalyst particles in a turbulent fluidization regime;

maintaining reaction temperature in the fluidized bed in the range from about 315° to 510° C.;

maintaining bed average density, measured at the bottom of the fluidized bed in the range from about 300 to 500 kg/m$^3$, at a pressure in the range from 400 kPa to 2500 kPa;

withdrawing a portion of coked catalyst from the reaction zone, oxidatively regenerating the withdrawn catalyst and returning regenerated catalyst to the fluidized bed at a rate sufficient to maintain a reaction severity index, expressed as the propane:propene weight ratio in the hydrocarbon product, in the range from about 0.2:1 to 5:1, whereby at least 90% of ethene and propene in the feedstock is converted to $C_4$+hydrocarbons.

6. The process of claim 5 wherein the active catalyst consists essentially of pore pentasil zeolite having an apparent alpha value of about 3 to 80, and average particle size of about 20 to 100 microns, and the reactor catalyst inventory includes at least 10 weight percent fine particles having a particle size less than 32 microns.

7. A process for oligomerization of propene-enriched light hydrocarbon feedstock containing at least 2 mol % ethene and having molar ratio of $C_3:C_2$ alkene of about 2:1 to 40:1 to produce heavier hydrocarbon products comprising isobutane and olefinic $C_5$+ gasoline wherein the feedstock is contacted under conversion conditions with a fluidized bed of medium pore shape selective catalyst particles in a vertical reactor column having a turbulent reaction zone, comprising:

maintaining a fluidized catalyst bed of particulate solid acid metallosilicate catalyst having an average density, measured at the bottom of the reaction zone, in the range from about 300 to 500 kg/m$^3$, at a pressure in the range from 410 kPa to 2500 kPa and a temperature in the range from about 315 to 510° C., by passing feedstock gas upwardly through the reaction zone while maintaining a superficial velocity greater than that at which slug flow breaks down but less than transport velocity for the average catalyst particle; and withdrawing a portion of coked catalyst from the reaction zone, oxidatively regenerating the withdrawn catalyst and returning regenerated catalyst to the reaction zone at a rate sufficient to maintain a reaction severity index expressed as the propane:propene weight ratio in the hydrocarbon product at about 0.2:1 to 5:1 measured in the absence of added propane, hereby at least 70% of ethene and propene in the feedstock is converted and increased yield of $C_4$+hydrocarbon product is achieved.

8. The process of claim 7 wherein the catalyst particles comprise about 5 to 95 weight percent aluminosilicate ZSM-5 zeolite in which the silica:alumina molar ratio is in the range from about 20:1 to about 200:1 and have a crystal size of about 0.02-2 microns.

9. The process of claim 7 wherein the superficial feedstock vapor velocity is about 0.3–2m/sec; the reaction temperature is about 315° to 510° C.; the weight hourly feedstock space velocity (based on olefin equivalent and total reactor catalyst inventory) is about 0.1 to 5.

10. The process of claim 7 wherein the catalyst consists essentially of a medium pore pentasil zeolite having an apparent alpha value of about 3 to 80, and average particle size of about 20 to 100 microns, the reactor catalyst inventory includes at least 10 weight percent fine particles having a particle size less than 32 microns.

11. The process of claim 7 wherein said feedstock consists essentially of $C_1$–$C_4$ light hydrocarbon cracking gas, and wherein olefin partial pressure in the feedstock is at least 50 kPa.

12. The process of claim 7 wherein $C_4$−hydrocarbon product is separated from the $C_5$+product and is recycled back to the reactor at a recycle ratio of 0.1:1 to 5:1 mol/mol to fresh feed.

13. The process of claim 7 wherein the reactor column contains vertical, horizontal, or a combination of vertical and horizontal heat exchanger tubes to remove reaction heat and control reaction temperature.

14. The process of claim 13 wherein the heat exchange tubes reduce effective reactor hydraulic diameter, decrease radial and axial mixing in the reactor, and improve reactor efficiency, whereby heat of reaction removal and reactor temperature control are enhanced by controlling feed temperature by heat exchange with reactor effluent and/or a supplemental heater.

15. The process of claim 7 wherein the feedstock comprises ethylenic FCC fuel gas enriched with a propane-propylene FCC byproduct stream and wherein hydrocarbon gas product is measured to determine propane:propene ratio and reaction severity conditions are adjusted to maintain the propane:propene weight ratio from about 0.2:1 to 5:1 after accounting for added propane.

16. The process of claim 7 wherein the catalyst consists essentially of siliceous aluminosilicate acid zeolite having the structure of ZSM-5 zeolite and a silica:alumina ratio in the range from about 25:1 to 70:1.

* * * * *